United States Patent
Mills

[11] Patent Number: 5,807,248
[45] Date of Patent: Sep. 15, 1998

[54] MEDICAL MONITORING PROBE WITH MODULAR DEVICE HOUSING

[75] Inventor: Michael A. Mills, Golden, Colo.

[73] Assignee: Ohmeda Inc., Liberty Corner, N.J.

[21] Appl. No.: 648,331

[22] Filed: May 15, 1996

[51] Int. Cl.[6] .................................................... A61B 5/00
[52] U.S. Cl. .......................... 600/322; 600/310; 600/323
[58] Field of Search .................................... 128/633, 639, 128/664, 665; 29/592.1, 422, 445, 464; 600/310, 311, 315, 316, 322–324, 326, 328, 344

[56] References Cited

U.S. PATENT DOCUMENTS

| | | | |
|---|---|---|---|
| 5,069,213 | 12/1991 | Polczynski | 128/633 |
| 5,094,240 | 3/1992 | Muz | 128/633 |
| 5,237,994 | 8/1993 | Goldberger | 128/633 |
| 5,465,714 | 11/1995 | Scheuing | 128/633 |
| 5,469,845 | 11/1995 | DeLonzor et al. | 128/665 |

FOREIGN PATENT DOCUMENTS 0435 500 A1  10/1990  European Pat. Off. .
WO 9412096 A  6/1994  WIPO .
WO 94 27494  12/1994  WIPO .

OTHER PUBLICATIONS

Hecht, "Second Optics, " Edition, Addison–Wesley Publishing Company, Reading, Massachusetts, 1987, pp. 10 and 94–96.

*Primary Examiner*—Jennifer Bahr
*Assistant Examiner*—Bryan K. Yarnell

[57] ABSTRACT

The manufacture of the electronics component of the probe is simplified by using an integral lead frame on which is mounted all of the passive and active elements so that the entire electronics module can be assembled independent of the housing in a simplified form prior to integration into the housing. The lead frame provides not only the electrical interconnections but the support and positioning of the various light emitting elements that comprise the electronics of the probe. The remaining segment of the manufacturing process is simplified since the workers do not have to assemble multiple diverse elements to create the device housing. The light reflecting and lens assemblies lock together and enclose an epoxy material which encapsulates the electronics elements and provides improved optical transmissivity of the generated light.

11 Claims, 3 Drawing Sheets

MEDICAL MONITORING PROBE WITH MODULAR DEVICE HOUSING

FIELD OF THE INVENTION

This invention relates to medical monitoring probes and, in particular, to a probe having a housing which is constructed of modular elements which function to enclose and encapsulate a lead frame on which is mounted the active and passive electronics elements.

PROBLEM

It is a problem in the field of medical monitoring probes to manufacture a probe that is rugged, efficient, and yet inexpensive and simple to manufacture. It is important that the probe be either inexpensive so that it can be disposable after one use or able to be cleaned so that it can be used for many patient applications. If the probe is reusable, then the active elements contained therein that perform the sensing and measuring functions must be protected from the ambient environment. A significant factor that is relevant to probe manufacturing is that the cost of manufacture is proportional to the number of components that must be assembled to manufacture the probe. Existing hard shell probes typically comprise a plurality of different housing elements that must be assembled around the wiring and a number of discrete components that comprise the sensor electronics of the probe. Therefore, the manufacturing and assembly of the probe is a fairly labor intensive operation with the worker having to electrically interconnect the various components to the wiring contained within the probe and then place the assembled wiring in a portion of the housing that encapsulates the probe. This partially assembled probe requires the addition of one or more additional housing elements to complete the assembly thereof. This present method of assembling probes and the probe design used in this process produce high quality probes but are relatively expensive to manufacture. A reduction in the number of elements required to manufacture a probe and/or a simplification of the manufacturing process in assembling the probe can represent significant cost savings to the probe manufacturer. Therefore, minor advances in probe architecture and manufacturing techniques reap large benefits.

SOLUTION

The above described problems are solved and a technical advance achieved in the field by the medical monitoring probe of the present invention. This probe makes use of a device housing which is assembled with a minimal number of modular pieces to enclose wiring and electronics that are mounted on a lead frame to create a unitary structure that simplifies the manufacture of the probe. By making use of a simplified modular device housing structure, the cost of the probe is significantly reduced since the entire device housing of the probe consists of interlocking molded elements.

The manufacture of the electronics component of the probe is simplified by using an integral lead frame on which is mounted all of the passive and active elements so that the entire electronics module can be assembled independent of the housing in a simplified form prior to integration into the housing. The lead frame provides not only the electrical interconnections but the support and positioning of the various light emitting and coding elements that comprise the electronics of the probe. The remaining segment of the manufacturing process is simplified since the workers do not have to assemble multiple diverse elements to create the device housing. The light reflecting and lens assemblies lock together and enclose an epoxy material which encapsulates the electronics elements and provides improved optical transmissivity of the generated light.

The assembly of the probe is therefore reduced to placement of the various elements on the lead frame and the bonding of these elements together to form the integral electronics structure which is then placed in one of the modular device housings in the position defined by the layout of the housing so that the elements of the integral lead frame are precisely positioned therein. This simplified, efficient method of manufacture with reduced number of parts reduces the costs of the probe by minimizing the labor content and the assembly thereof and reducing the cost of the components used to manufacture the probe.

DETAILED DESCRIPTION

Figure 1:
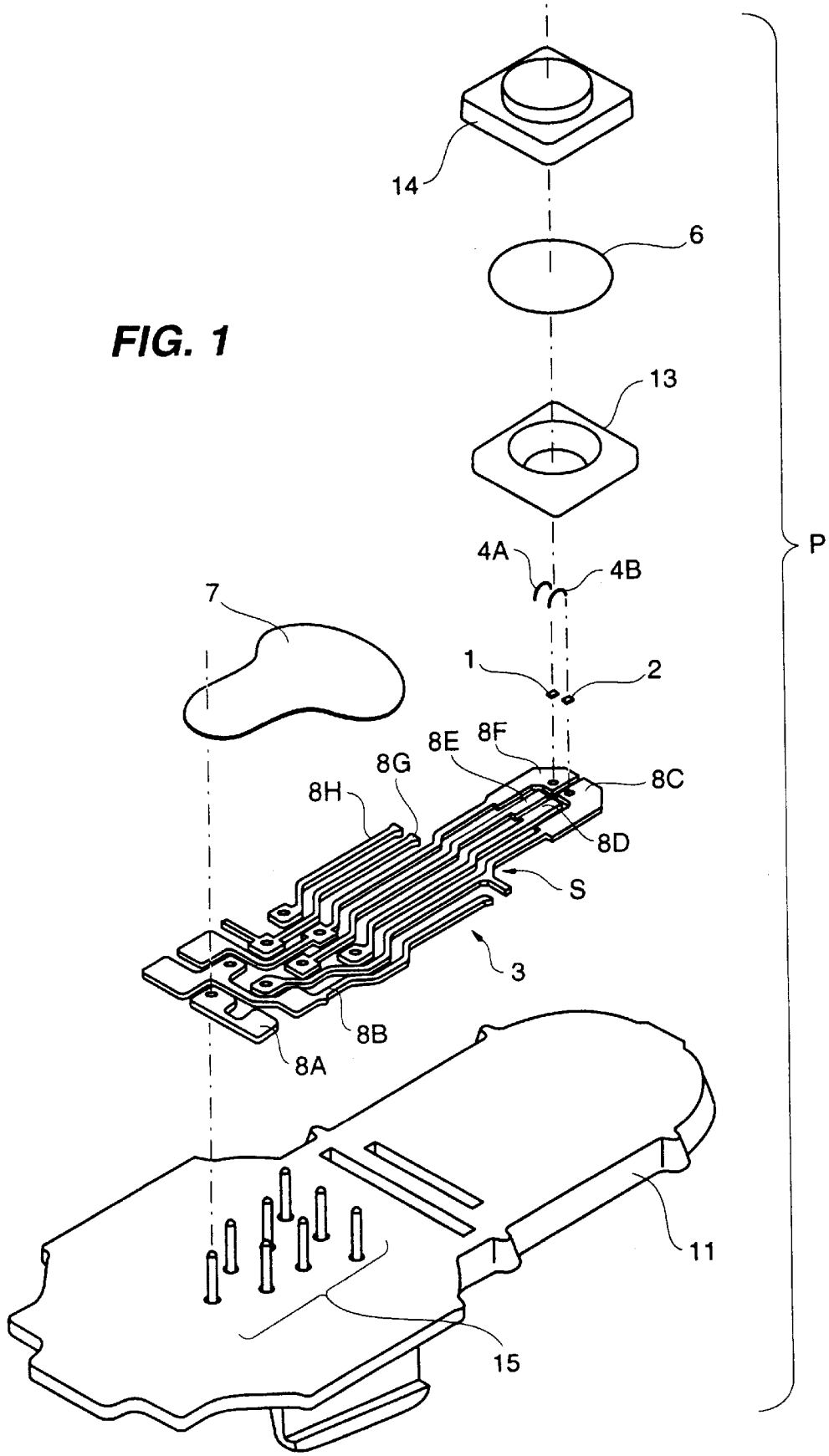
FIG. 1 illustrates an exploded perspective view of the probe of the present invention.
Figure 2:
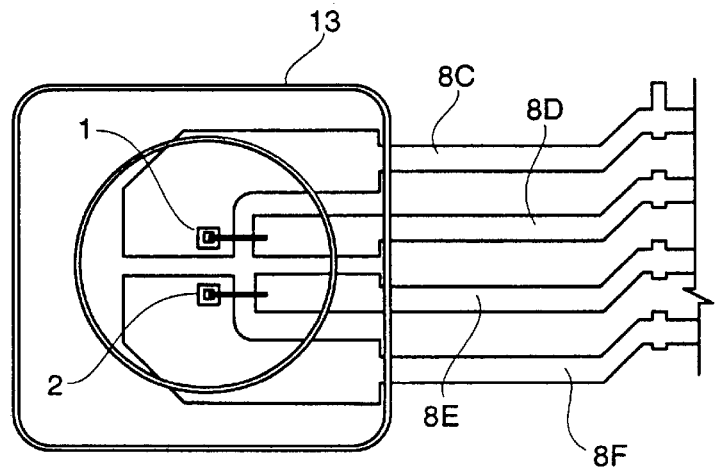
FIG. 2 illustrates a top view of the light emitter assembly portion of the probe electronics assembly.
Figure 3:
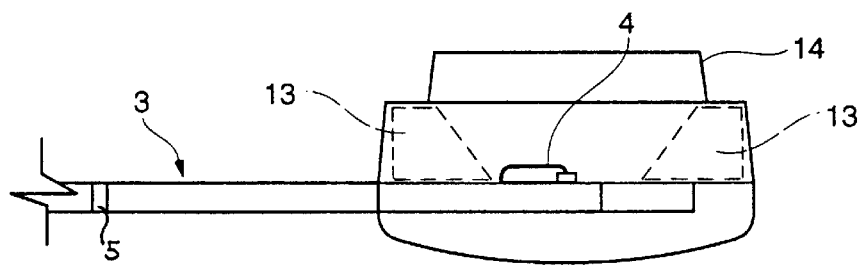
FIG. 3 illustrates a side view of the assembled electronics assembly.

Any improvements, however incremental, in the design and manufacturability of a probe in the field of medical monitoring instruments result in significant cost savings. The apparatus of the present invention consists of a device housing which is assembled with a minimal number of modular pieces to enclose wiring and electronics that are mounted on a lead frame to create a unitary structure that simplifies the manufacture of the probe. FIG. 1 illustrates the probe module in a perspective exploded view while FIGS. 2 and 3 provide views of additional details of the probe assembly. The apparatus of the present invention represents an architecture in which the configuration of elements are cooperatively operative to solve the problems of existing medical monitoring instrument probes.

PHOTOPLETHYSMOGRAPHIC PROBE APPLICATION

A pulse oximeter instrument is frequently used to monitor the condition of a patient in a hospital setting. The pulse oximeter instrument noninvasively measures the oxygen saturation of the arterial blood and produces a human readable display that indicates both the patient's heart rate and the oxygen saturation of the arterial blood. These readings are important to enable the medical staff to determine whether the patient's respiratory system is functioning properly, supplying sufficient oxygen to the blood.

A pulse oximeter instrument operates by use of a probe that transilluminates an appendage of the patient (such as a finger, earlobe, or the nasal septum) that is rich in arterial blood and measuring the amount of light that is absorbed by the pulsatile portion of the arterial blood to thereby determine oxygen saturation of the arterial blood. The pulse oximeter instrument makes use of a plurality of light-emitting devices, each of which transmits light at a predetermined wavelength, which wavelengths are selected such that at least one is highly absorbed by oxygenated hemoglobin in the arterial blood and at least one is highly absorbed by reduced hemoglobin in the arterial blood. The amount of absorption of the light beams generated by these light emitting devices that are located in the probe is a measure of the relative concentration of the oxygenated and reduced hemoglobin in the arterial blood. The absorption of the light that is being transmitted through the appendage of the patient includes a constant portion that is a result of skin, bone, steady-state (venous) blood flow and light loss due to various other factors. The pulsatile component of absorption is due to the pulsatile arterial blood flow and is a small fraction of the received signal and is used by the pulse oximeter instrument to perform its measurements.

The measurements are computed by periodically sampling the output of the light detector located in the probe to determine the incremental change in absorption of the various wavelengths of light transmitted through the appendage of the patient. These incremental changes in light absorption are then used to compute the oxygen saturation of the arterial blood as well as the patient's pulse rate. Since the pulsatile component of the signals received by the light detector represent only a small fraction of the incident light, it is important that the incident light be of significant magnitude to result in transmitted signals that have sufficient amplitude to provide accurate readings. In addition, the light-emitting devices and the light detector must be placed in intimate contact with the skin of the patient on opposite sides of the appendage (or on the same side of the appendage in reflectance probes) to obtain the most accurate readings. The probe design must therefore be such that it inherently accommodates variations in size and shape of the patient's appendage and also enables the medical staff to simply align the probe to obtain the maximum readings. These stringent requirements are difficult for existing probes to comply with and increase the manufacturing cost of the probes, which may be disposable elements.

PROBE IMPLEMENTATION

FIG. 1 illustrates a perspective exploded view of the electronics assembly portion of the probe P of the present invention. The electronics assembly is attached to a connector shell element 11 which is a portion of the probe housing. The connector shell element 11 includes a plurality of holes formed therein to receive a number of pins 15 which comprise the electrical conductors of the connector. The pins 15 are typically molded into the connector shell element 11 to insure their precise positioning and secure mounting therein. A lead frame 3 formed of a plurality of conductors 8A–8H provides the electrical interconnection of the active and passive elements which comprise the electronics portion of the probe P. In particular, eight pins 15 are shown in FIG. 1, but the number and precise placement of these elements are a function of the specific implementation of the electronics elements contained in the probe P. For the purpose of illustration, the eight pins 15 comprise a predetermined pattern of conductors which mate with a like number and configuration of apertures formed in the eight conductors 8A–8H of lead frame 3. The lead frame 3 therefore fits on top of the pins 15 and is soldered thereto. At the other end of the lead frame 3, distal from the connector pins 15 are mounted a plurality of light emitting devices, with two light emitting devices 1, 2 being shown in FIG. 1 as an illustration. The light emitting devices 1, 2 are each connected to two corresponding conductors 8C, 8D and 8E, 8F, respectively, of the lead frame 3. As shown in the illustration in FIG. 2, the light emitting devices 1, 2 are individually placed on top of a corresponding one of the lead frame conductors 8C, BF on a mounting pad area contained therein. The other of the two electrical conductors 8D, 8E is connected to the light emitting devices 1, 2 by means of a wire bond 4A, 4B which are electrically connected to the light emitting device 1, 2 at one end and a lead frame conductor 8D, 8E at the other end.

LIGHT REFLECTING ELEMENT AND LENS ASSEMBLY

Figure 4:
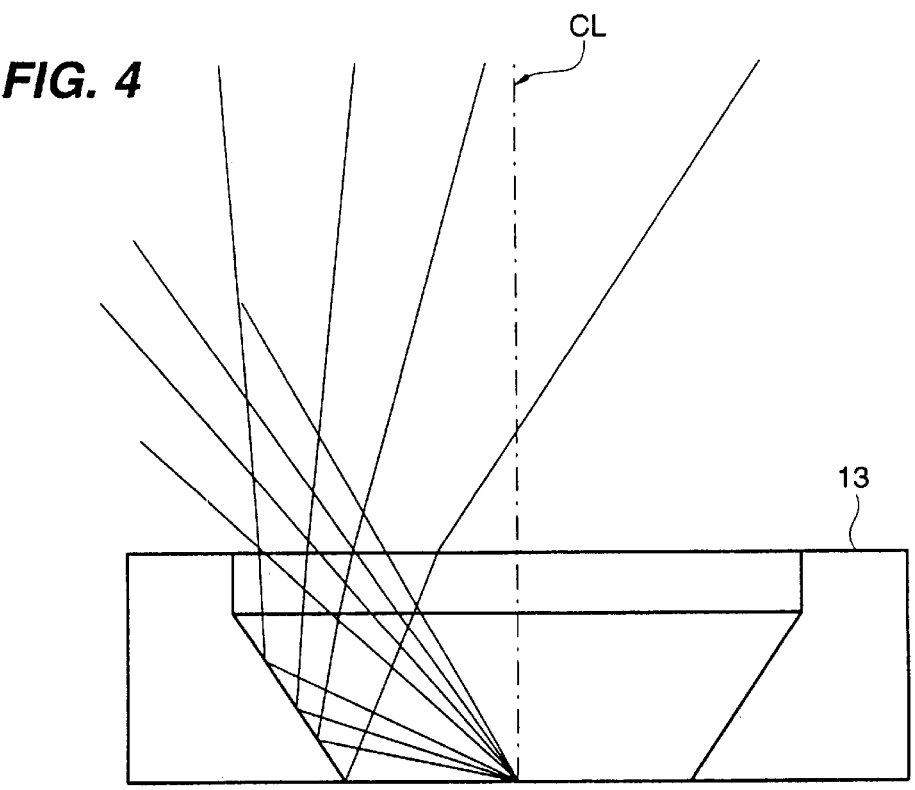
FIG. 4 illustrates a side cross-section view of the light reflecting apparatus.

The electronics subassembly comprising the lead frame 3 with the attached coding resistor 5 and the light emitting devices 1,2 are joined with the light reflecting 13 and lens assembly 14 elements to form the electronics assembly, as shown in side view in FIG. 3. The light reflecting element 13 is added to this subassembly to increase the light transmissivity of the assembly, as is shown by the side cross-section view of FIG. 4. In particular, the light reflector 13 is a block of material having an aperture formed therein which is in the form of a geometrically shaped section which serves to receive light from the light emitting devices 1, 2 of the probe P and redirect this light in the direction of the perfused tissue to be illuminated, as shown in FIG. 4 by the plurality of lines representative of rays of light emitted by the light emitting devices 1, 2. The shape of the aperture formed in the light reflective element 13 can be any shape which functions as described and can be selected from the geometric shapes including, but not limited to: truncated conical section, semi-spherical section, elliptical section, flat angle. For the purpose of this description, the truncated conical section is used, since this geometric shape has a high output and is low cost to manufacture.

The light reflective element 13 comprises a polycarbonate molding having an interior conical surface of roughly 45°, on which conical face a silver coating is deposited. The silver coating also includes a dielectric overcoat, so that the surface reflectivity is optimized for 600–1000 nm to obtain 90% reflectivity of the light generated by the light emitting devices 1, 2. The light reflective element 13 is held in place by the application of a compound of clear epoxy 6 which is placed inside of the cup formed by the light reflective element 13. This combination of elements is then placed in position over the lens assembly 14 which is oriented in an inverted position, and partially filled with clear epoxy. The lens assembly comprises a Lexan® material which has a light transmissivity characteristic that enables the majority of the light produced by the light emitting devices 1, 2 to be passes through the lens assembly 14. The subassembly is then placed on the epoxy filled lens 14, with this additional epoxy filling any voids so that the interstitial space between the light emitting devices 1, 2 and the interior surface of the lens assembly 1 4 is devoid of air space. The inverted assembly has a predetermined amount of clear epoxy added to the back side surface thereof to complete the potting process. The assembly is then treated to cure the epoxy and form a solid light transmissive fill for the probe P. The light emitting devices 1, 2 are secured in place by the epoxy fill and are also hermetically sealed therein, protected from the ambient environment. The shape of the light reflective element 13 and the lens assembly 14 are mating, such that the two elements fit precisely together. In addition, the lens assembly 14 includes a shoulder formed therein to conform to a ledge formed in the sensor housing. Thus, the shoulder formed in the lens assembly 14 mates with the ledge formed in the housing to precisely position the light emitting devices 1, 2 and provide an integral fit therebetween.

In addition, a coating of epoxy material 7 is added to the lead frame 3 to protect and encapsulate the exposed electrical conductors 8A–8H. The coating of epoxy material 7 covers the configuration of connector pins 15 and may also optionally be used to cover the coding resistor 5. The extent of the coating of epoxy material 7 is typically limited by the shoulder S formed in the lead frame 3 adjacent to the connector pins 15.

METHOD OF MANUFACTURE OF THE PROBE

Figure 5:
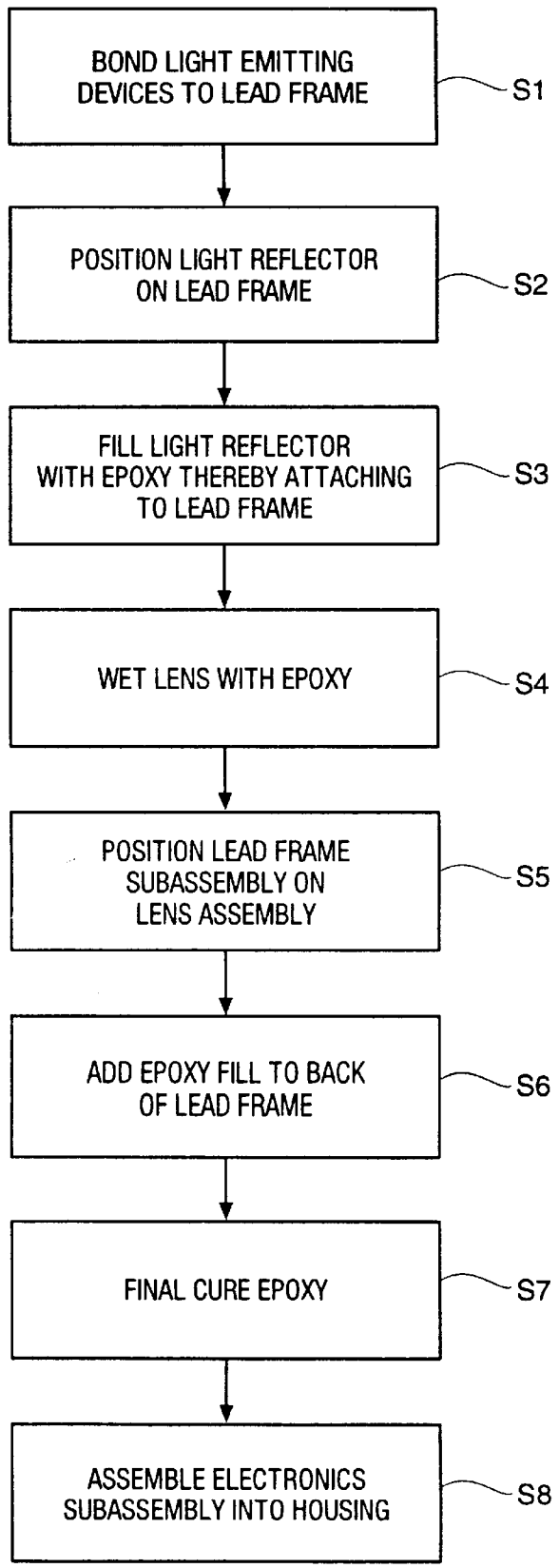
FIG. 5 illustrates in flow diagram form the steps taken to assemble the probe.

The method of manufacturing the probe P is described in flow diagram form in FIG. 5. This process comprises wire bonding the dies that contain light emitting devices 1, 2 to the lead frame 3 at step S1. The lead frame 3 is then equipped at step S2 with the light reflective element 13 and epoxy is added to the light reflective element 13 at step S3 to fill the light reflective element 13 and partially cured to adhere it in place on the lead frame 3. At step S4, the lens assembly 14 is placed in a fixture (not shown) and epoxy added thereto. At step S5 the lead frame subassembly is placed over the lens assembly 14 and, at step S6, epoxy is added to the exposed back surface of the lead frame 3 to ensure compete fill of the space within the probe electronics subassembly. The final curing of the epoxy is performed at step S7 and the assembly of the probe electronics is completed at step S8 with the placement of the electronics subassembly in the final probe housing.

SUMMARY

The manufacture of the electronics component of the probe is simplified by using an integral lead frame on which is mounted all of the passive and active elements so that the entire electronics module can be assembled independent of the housing in a simplified form prior to integration into the housing. The lead frame provides not only the electrical interconnections but the support and positioning of the various light emitting and coding elements that comprise the electronics of the probe. The remaining segment of the manufacturing process is simplified since the workers do not have to assemble multiple diverse elements to create the device housing. The light reflecting and lens assemblies lock together and enclose an epoxy material which encapsulates the electronics elements and provides improved optical transmissivity of the generated light. This structure and process can be used to form probes of different configuration and content. For example, a coding resistor can be included in the probe, as is well known in the art, to define the light transmission characteristics of the light emitting devices via the impedance value of the coding resistor. In addition, more than two light emitting devices can be used in this probe design and the use of two devices is for the purpose of illustrating the concepts of the invention.

While a specific embodiment of the electronics assembly has been disclosed herein, it is expected that other implementations of this apparatus which utilize the inventive concepts taught herein can be devised, which alternative embodiments are intended to fall within the scope of the claims contained herein.

I claim:

1. An electronics assembly of light emitting devices for use in a probe module, affixable to an appendage of a patient, for illuminating perfused tissue in said appendage to measure light absorption of blood analytes contained in said perfused tissue, comprising:

a lead frame comprising a plurality of electrical conductors formed into a predetermined pattern;

light emitting means mounted on said lead frame and in electrical communication with said electrical conductors;

light reflective means mounted on said lead frame and encircling said light emitting means for directing beams of light generated by said light emitting means toward said perfused tissue; and lens means formed prior to mating to mate with said light reflective means and mounted in mating fashion thereon for transmitting said beams of light generated by said light emitting means and reflected by said light reflective means toward said perfused tissue wherein said lens means and said light reflective means form a space therebetween.

2. The electronics assembly of claim 1 further comprising:

fill means occupying substantially all of said space that exists between said lens means and said light reflective means for encapsulating said light emitting means and for securing said light emitting means, said light reflective means and said lens means in a predetermined relation to each other.

3. The electronics assembly of claim 2 wherein said fill means comprises an optically transmissive medium for transmitting said beams of light generated by said light emitting means to said lens means.

4. The electronics assembly of claim 3 wherein said fill means comprises a material having substantially the same optical characteristics as said lens means.

5. The electronics assembly of claim 1 wherein said light emitting means comprises:

at least two light emitting devices, each of which produces a beam of light at a predefined wavelength.

6. The electronics assembly of claim 1 wherein said light reflective means comprises:

a block of material having formed therein an aperture whose interior surface comprises a truncated cone, whose narrower end is proximate said light emitting means and encircles said light emitting means.

7. The electronics assembly of claim 6 wherein said interior surface of said aperture is coated with a light reflective material.

8. The electronics assembly of claim 6 wherein said interior surface of said aperture is of angle to collect a majority of light emitted by said light emitting means into a beam for transmission to said perfused tissue.

9. The electronics assembly of claim 1 wherein said light reflective means comprises:

a block of material having formed therein an aperture whose interior surface comprises a geometric shape selected from the class of geometric shapes including: spherical, elliptical, flat angle, truncated cone, and said aperture having a narrow end and a wide end, said narrow end being proximate said light emitting means and encircling said light emitting means.

10. The electronics assembly of claim 9 wherein said interior surface of said aperture is coated with a light reflective material.

11. The electronics assembly of claim 9 wherein said interior surface of said aperture collects a majority of light emitted by said light emitting means into a beam for transmission to said perfused tissue.

* * * * *